(12) United States Patent
Gandhi et al.

(10) Patent No.: US 7,198,613 B2
(45) Date of Patent: Apr. 3, 2007

(54) APPARATUS FOR DEPLOYMENT OF MICRO-COIL USING A CATHETER

(75) Inventors: Deepak Gandhi, San Jose, CA (US); Kamal Ramzipoor, Union City, CA (US)

(73) Assignee: Micrus Endovascular Corporation, San Jose, CA (US)

(*) Notice: Subject to any disclaimer, the term of this patent is extended or adjusted under 35 U.S.C. 154(b) by 237 days.

(21) Appl. No.: 11/020,936

(22) Filed: Dec. 22, 2004

(65) Prior Publication Data

US 2005/0113864 A1    May 26, 2005

Related U.S. Application Data

(63) Continuation of application No. 10/290,777, filed on Nov. 7, 2002, now Pat. No. 6,966,892, which is a continuation of application No. 09/501,466, filed on Feb. 9, 2000, now Pat. No. 6,478,773.

(51) Int. Cl.
  *A61F 7/12* (2006.01)
  *A61F 11/00* (2006.01)
  *A61M 29/00* (2006.01)

(52) U.S. Cl. .................. 604/114; 606/108; 606/194

(58) Field of Classification Search ............ 604/93.01, 604/95.05, 113, 114, 533; 606/108, 191, 606/192, 194, 195, 198; 623/1.23, 1.11, 623/1.12
See application file for complete search history.

(56) References Cited

U.S. PATENT DOCUMENTS

| | | |
|---|---|---|
| 1,341,052 A | 5/1920 | Gale |
| 2,078,182 A | 4/1937 | MacFarland |
| 2,549,335 A | 4/1951 | Rahthus |
| 3,334,629 A | 8/1967 | Cohn |
| 3,485,234 A | 12/1969 | Stevens |
| 3,649,224 A | 3/1972 | Anderson et al. |
| 3,868,956 A | 3/1975 | Alfidi et al. |
| 4,327,734 A | 5/1982 | White, Jr. |
| 4,341,218 A | 7/1982 | Ü |
| 4,346,712 A | 8/1982 | Handa et al. |

(Continued)

FOREIGN PATENT DOCUMENTS

DE    4102550 A1    8/1991

(Continued)

OTHER PUBLICATIONS

US 5,766,161, 07/1998, Globerman (withdrawn).

(Continued)

*Primary Examiner*—Kevin C. Sirmons
*Assistant Examiner*—Benjamin Huh
(74) *Attorney, Agent, or Firm*—Fulwider Patton LLP

(57) ABSTRACT

The apparatus for deployment of a therapeutic device such as a micro-coil detachably mounts the therapeutic device to a distal portion of a pusher member. In one embodiment, the therapeutic device is detachably mounted to the distal portion of the pusher member by a tubular collar that can be heated by a heater such as an electrical resistance coil to expand the collar and release and deploy the therapeutic device. The apparatus for deployment of a therapeutic device such as a micro-coil may also provide for a pusher member and a connector fiber for securing the therapeutic device to the pusher member. The connector fiber passes through a heater within the distal portion of the pusher member, for heating and breaking the connector fiber to release the therapeutic device when a desired placement of the therapeutic device within the vasculature is achieved.

11 Claims, 4 Drawing Sheets

U.S. PATENT DOCUMENTS

| | | |
|---|---|---|
| 4,402,319 A | 9/1983 | Handa et al. |
| 4,441,495 A | 4/1984 | Hicswa |
| 4,494,531 A | 1/1985 | Gianturco |
| 4,512,338 A | 4/1985 | Balko et al. |
| 4,545,367 A | 10/1985 | Tucci |
| 4,553,545 A | 11/1985 | Maass et al. |
| 4,611,594 A | 9/1986 | Grayhack et al. |
| 4,629,458 A | 12/1986 | Pinchuk |
| 4,638,803 A | 1/1987 | Rand |
| RE32,348 E | 2/1987 | Pevsner |
| 4,655,771 A | 4/1987 | Wallsten |
| 4,670,286 A | 6/1987 | Nyilas et al. |
| 4,718,907 A | 1/1988 | Karwoski et al. |
| 4,732,152 A | 3/1988 | Wallstén et al. |
| 4,748,986 A | 6/1988 | Morrison et al. |
| 4,768,507 A | 9/1988 | Fischell et al. |
| 4,795,458 A | 1/1989 | Regan |
| 4,798,606 A | 1/1989 | Pinchuk |
| 4,800,882 A | 1/1989 | Gianturco |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,873,978 A | 10/1989 | Ginsburg |
| 4,950,258 A | 8/1990 | Kawai et al. |
| 4,954,126 A | 9/1990 | Wallsten |
| 4,957,479 A | 9/1990 | Roemer |
| 4,957,501 A | 9/1990 | Lahille et al. |
| 4,990,155 A | 2/1991 | Wilkoff |
| 4,994,069 A | 2/1991 | Ritchart et al. |
| 4,994,071 A | 2/1991 | MacGregor |
| 5,002,556 A | 3/1991 | Ishida et al. |
| 5,015,253 A | 5/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,037,377 A | 8/1991 | Alonso |
| 5,041,084 A | 8/1991 | DeVries et al. |
| 5,041,126 A | 8/1991 | Gianturco |
| 5,061,275 A | 10/1991 | Wallstén et al. |
| 5,064,435 A | 11/1991 | Porter |
| 5,071,407 A | 12/1991 | Termin et al. |
| 5,104,404 A | 4/1992 | Wolff |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,364 A | 7/1992 | Palermo et al. |
| 5,133,731 A | 7/1992 | Butler et al. |
| 5,133,732 A | 7/1992 | Wiktor |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,152,784 A | 10/1992 | Tsilibary |
| 5,160,341 A | 11/1992 | Brenneman et al. |
| 5,171,273 A | 12/1992 | Silver et al. |
| 5,176,625 A | 1/1993 | Brisson |
| 5,176,661 A | 1/1993 | Evard et al. |
| 5,181,921 A | 1/1993 | Makita et al. |
| 5,183,085 A | 2/1993 | Timmermans |
| 5,186,992 A | 2/1993 | Kite, III |
| 5,188,621 A | 2/1993 | Samson |
| 5,192,290 A | 3/1993 | Hilal |
| 5,197,977 A | 3/1993 | Hoffman, Jr. et al. |
| 5,203,772 A | 4/1993 | Hammerslag et al. |
| 5,211,658 A | 5/1993 | Clouse |
| 5,217,484 A | 6/1993 | Marks |
| 5,222,969 A | 6/1993 | Gillis |
| 5,222,970 A | 6/1993 | Reeves |
| 5,224,953 A | 7/1993 | Morgentaler |
| 5,226,911 A | 7/1993 | Chee et al. |
| 5,226,913 A | 7/1993 | Pinchuk |
| 5,228,453 A | 7/1993 | Sepetka |
| 5,234,456 A | 8/1993 | Silvestrini |
| 5,238,004 A | 8/1993 | Sahatjian et al. |
| 5,250,071 A | 10/1993 | Palermo |
| 5,256,146 A | 10/1993 | Ensminger et al. |
| 5,258,042 A | 11/1993 | Mehta |
| 5,261,916 A | 11/1993 | Engelson |
| 5,275,173 A | 1/1994 | Samson et al. |
| 5,304,194 A | 4/1994 | Chee et al. |
| 5,312,415 A | 5/1994 | Palermo |
| 5,314,472 A | 5/1994 | Fontaine |
| 5,322,501 A | 6/1994 | Mahmud-Durrani |
| 5,336,205 A | 8/1994 | Zenzen et al. |
| 5,341,818 A | 8/1994 | Abrams et al. |
| 5,342,387 A | 8/1994 | Summers |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,368,049 A | 11/1994 | Raman et al. |
| 5,373,856 A | 12/1994 | Grenouillet |
| 5,382,259 A | 1/1995 | Phelps et al. |
| 5,383,887 A | 1/1995 | Nadal |
| 5,395,390 A | 3/1995 | Simon et al. |
| 5,405,377 A | 4/1995 | Cragg |
| 5,409,015 A | 4/1995 | Palermo |
| 5,411,475 A | 5/1995 | Atala et al. |
| 5,413,597 A | 5/1995 | Krajicek |
| 5,415,664 A | 5/1995 | Pinchuk |
| 5,417,708 A | 5/1995 | Hall et al. |
| 5,423,829 A | 6/1995 | Pham et al. |
| 5,433,723 A | 7/1995 | Lindenberg et al. |
| 5,441,516 A | 8/1995 | Wang et al. |
| 5,443,478 A | 8/1995 | Purdy |
| 5,443,498 A | 8/1995 | Fontaine |
| 5,484,449 A | 1/1996 | Amundson et al. |
| 5,500,013 A | 3/1996 | Buscemi et al. |
| 5,514,115 A | 5/1996 | Frantzen et al. |
| 5,514,176 A | 5/1996 | Bosley, Jr. |
| 5,520,194 A | 5/1996 | Miyata et al. |
| 5,522,822 A | 6/1996 | Phelps et al. |
| 5,522,836 A | 6/1996 | Palermo |
| 5,523,092 A | 6/1996 | Hanson et al. |
| 5,527,336 A | 6/1996 | Rosenbluth et al. |
| 5,540,701 A | 7/1996 | Sharkey et al. |
| 5,549,624 A | 8/1996 | Mirigian et al. |
| 5,562,641 A | 10/1996 | Flomenblit et al. |
| 5,562,698 A | 10/1996 | Parker |
| 5,569,245 A | 10/1996 | Guglielmi et al. |
| 5,578,074 A | 11/1996 | Mirigian |
| 5,582,619 A | 12/1996 | Ken |
| 5,603,694 A | 2/1997 | Brown et al. |
| 5,607,445 A | 3/1997 | Summers |
| 5,609,627 A | 3/1997 | Goicoechea et al. |
| 5,613,981 A | 3/1997 | Boyle et al. |
| 5,624,461 A | 4/1997 | Mariant |
| 5,637,113 A | 6/1997 | Tartaglia et al. |
| 5,638,827 A | 6/1997 | Palmer et al. |
| 5,639,277 A | 6/1997 | Mariant et al. |
| 5,643,254 A | 7/1997 | Scheldrup et al. |
| 5,643,339 A | 7/1997 | Kavteldaze et al. |
| 5,645,564 A | 7/1997 | Northrup et al. |
| 5,649,949 A | 7/1997 | Wallace et al. |
| 5,653,726 A | 8/1997 | Kieturakis |
| 5,653,727 A | 8/1997 | Wiktor |
| 5,666,968 A | 9/1997 | Imran et al. |
| 5,667,522 A | 9/1997 | Flomenblit et al. |
| 5,676,697 A | 10/1997 | McDonald |
| 5,690,643 A | 11/1997 | Wijay |
| 5,690,666 A | 11/1997 | Berenstein et al. |
| 5,690,671 A | 11/1997 | McGurk et al. |
| 5,693,085 A | 12/1997 | Buirge et al. |

| | | |
|---|---|---|
| 5,702,373 A | 12/1997 | Samson |
| 5,702,414 A | 12/1997 | Richter et al. |
| 5,713,907 A | 2/1998 | Hogendijk et al. |
| 5,722,989 A | 3/1998 | Fitch et al. |
| 5,725,546 A | 3/1998 | Samson |
| 5,733,329 A | 3/1998 | Wallace et al. |
| 5,743,905 A | 4/1998 | Eder et al. |
| 5,746,765 A | 5/1998 | Kleshinski et al. |
| 5,746,769 A | 5/1998 | Ton et al. |
| 5,749,883 A | 5/1998 | Halpern |
| 5,749,891 A | 5/1998 | Ken et al. |
| 5,749,894 A | 5/1998 | Engelson |
| 5,749,918 A | 5/1998 | Hogendijk et al. |
| 5,749,921 A | 5/1998 | Lenker et al. |
| 5,788,653 A | 8/1998 | Lorenzo |
| 5,797,957 A | 8/1998 | Palmer et al. |
| 5,800,455 A | 9/1998 | Palermo |
| 5,800,526 A | 9/1998 | Anderson et al. |
| 5,814,062 A | 9/1998 | Sepetka et al. |
| 5,824,059 A | 10/1998 | Wijay |
| 5,944,733 A | 8/1999 | Engelson |
| 5,947,963 A | 9/1999 | Guglielmi |
| 5,984,929 A | 11/1999 | Bashiri et al. |
| 5,989,242 A | 11/1999 | Saadat et al. |
| 6,059,815 A | 5/2000 | Lee et al. |
| 6,224,610 B1 | 5/2001 | Ferrera |
| 6,296,622 B1 | 10/2001 | Debeer |

FOREIGN PATENT DOCUMENTS

| | | |
|---|---|---|
| EP | 0 183 372 A1 | 6/1986 |
| EP | 0 278 937 | 8/1988 |
| EP | 0 382014 A1 | 8/1990 |
| EP | 0 518 704 A1 | 12/1992 |
| EP | 0 627 201 A1 | 12/1994 |
| FR | 592.182 | 7/1925 |
| GB | 2 066 839 A | 7/1981 |
| WO | WO 92/14408 | 3/1992 |
| WO | WO 94/16629 | 4/1994 |
| WO | WO 95/18585 | 7/1995 |
| WO | WO 95/21592 | 8/1995 |
| WO | WO 97/48351 | 12/1997 |

OTHER PUBLICATIONS

Christos A. Athanasoulis, M.D., The New England Journal of Medicine, May 15, 1980, "Therapeutic Applications of Angiography" pp. 1117-1125 (1 of 2).

Christos A. Athanasoulis, M.D., The New England Journal of Medicine, May 22, 1980, "Therapeutic Applications of Angiography" pp. 1174-1179 (2 of 2).

Alex Berenstein, M.D. and Irvin I. Kricheff, M.D., "Catheter and Material Selection for Transarterial Embolization: Technical Considerations" Radiology, Sep. 1979; pp. 631-639.

O.A. Battista, et al. Journal of Applied Polymer Science 1967 "Colloidal Macromolecular Phenomena. Part II. Novel Microcrystals of Polymers" pp. 481-498.

Sadek K. Hilal, M.D. et al. Journal of Neurological Surgery "Therapeutic Percutaneous Embolization for Extra-Axial Vascular Lesions of the Head, Neck and Spine" Sep. 1975; pp. 275-287.

Stephen L. Kaufman, M.D. et al. Investigative Radiology, May-Jun. 1978, "Transcatheter Embolization with Microfibrillar Collagen in Swine"; pp. 200-204.

Ashok J. Kumar, et al., Journal of Neuroradiology (1982) "Preoperative Embolization of Hypervascular Head and Neck Neoplasms Using Microfibrillar Collagen", pp. 163-168.

Richard E. Latchaw, M.D. et al., Radiology (1979) "Polyvinyl Foam Embolization of Vascular and Neoplastic Lesions of the Head, Neck and Spine" pp. 669-679.

Stewart R. Reuter, M.D. et al. American Journal of Radiology, Sep. 1975, "Selective Arterial Embolization For Control of Massive Upper Gastrointestinal Bleeding" pp. 119-126.

Glenn H. Roberson, et al., American Journal of Radiology, Oct. 1979, "Therapeutic Embolization of Juvenile Angiofibroma" pp. 657-663.

Sidney Wallace, M.D. et al., Cancer, Oct. 1979, "Arterial Occlusion of Pelvic Bone Tumors"; pp. 322-325 & 661-663.

"Mechanical Devices for Arterial Occlusion" By C. Giantgurco, M.D., et al., Jul. 1975, pp. 428-435.

"Therapeutic Vascular Occlusion Utilizing Steel Coil Technique: Clinical Applications" By Sidney Wallace, et al., Am J. Roentgenol (1976); pp. 381-387.

"Transcatheter Intravascular Coil Occlusion of Experimental Arteriovenous Fistulas", By James H. Anderson, et al., Am. J. Roentgenol, Nov. 1977, pp. 795-798.

"'Mini' Gianturco Stainless Steel Coils For Transcatheter Vascular Occusion" By James H. Anderson, et al., From The Department of Diagnostic Radiology at the University of Texas System Cancer Center, Aug. 1978, pp. 301-303.

"A New Improved Coil For Tapered-Tip Catheter For Arterial Occlusion" By Vincent P. Chuang, M.D., et al., May 1980, pp. 507-509.

"Retrievable Gianturco-Coil Introducer" By Jeffrey Hawkins, Ronald G. Quisling, MD, J. Parker Mickle, MD, Irvin F. Hawkins, MD, From the Department of Radiology at the University of Florida Medical Center and Hawk Prototype Equipment 1986.

APPARATUS FOR DEPLOYMENT OF MICRO-COIL USING A CATHETER

RELATED APPLICATIONS

This is a continuation of Ser. No. 10/290,777, filed Nov. 7, 2002, now U.S. Pat. No. 6,966,892 which is a continuation of Ser. No. 09/501,466, filed Feb. 9, 2000, now Pat. No. 6,478,773.

BACKGROUND OF THE INVENTION

1. Field of the Invention

This invention relates generally to devices for interventional therapeutic treatment or vascular surgery for treatment of defects in the vasculature, and more particularly concerns a system and method for delivering intravascular interventional devices, such as for treatment of aneurysms.

2. Description of Related Art

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through a vessel making up that portion of the vasculature through the formation of an embolus, or are placed within an aneurysm stemming from the vessel to form such an embolus within the aneurysm. Stents can have a wide variety of configurations, but generally need to be placed and then released at a desired location within a blood vessel. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive coils.

The delivery of such vasoocclusive devices have typically been accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area of interest, such as an aneurysm.

One conventional releasable balloon catheter used to embolize vascular lesions has a tube portion made of a material such as a hydrophilic polymer, located between the catheter and the balloon, that can be melted by heating the tube, or can be dissolved in the blood when heated, and electrodes are provided for heating the tube. Another conventional technique for separating a balloon from a balloon catheter involves the melting and breaking of a connecting member between the balloon and the catheter body, when power is supplied to electrodes provided for heating the connecting member. When the connecting member is heated to temperatures of about 70° C. and slight tension is applied, the balloon can be separated from the main catheter body.

An implant delivery assembly is also known that is used for delivery of implants such as embolic coils, utilizing a shape memory decoupling mechanism activated when exposed to body temperature. A cooling solution is flushed through the catheter during introduction and placement of the implant in order to prevent premature release of the implant prior to the time that the implant is to be released. Another implant delivery assembly includes an electrical heating system for heating the coupling mechanism to a temperature at which the shape memory material returns to its original shape, to deploy the implant.

Another device is known in which a device to be implanted is detached by application of a high-frequency current which melts and severs a resin that is used to retain the device to be implanted until the device is to be deployed. In another known device, an electrolytically severable link is dissolved by activation of a power source electrically coupled to the electrolytically severable link to detach the device to be implanted.

In another conventional technique, a conductive guidewire delivers a high frequency current through the guidewire to melt and sever a joint to detach an implanted device from the guidewire. The patient is grounded during the procedure, and current is introduced via the guidewire, rather than with a two way current path.

Such devices that release the interventional device by melting or dissolving the intermediate section between the catheter tip and implanted device may cause thermal damage of surrounding tissues during detachment that can cause embolization in the bloodstream, and may also potentially release undesirable particles of materials into the bloodstream that can also cause embolization in the bloodstream. There is therefore a need for a precise method of deploying therapeutic interventional devices without compromising the position of the implant, without causing thermal damage to surrounding tissues, and without releasing undesirable particles of materials into the bloodstream and risking the formation of emboli in the bloodstream. The present invention meets these and other needs.

SUMMARY OF THE INVENTION

Briefly, and in general terms, the present invention provides for an apparatus for deployment of a therapeutic device such as a micro-coil using a catheter by connecting the therapeutic device to a distal portion of a pusher member. In one presently preferred embodiment, the therapeutic device is detachably mounted to the distal portion of the pusher member by a tubular collar that can be heated by a heater to expand the collar and release and deploy the therapeutic device. In another presently preferred embodiment, the therapeutic device is detachably mounted to the distal portion of the pusher member by a connector thread or fiber passing through a heater provided for heating and breaking the connector fiber to release the therapeutic device. In one presently preferred aspect, the heater is advantageously contained substantially within the distal portion of the pusher member, which provides a sufficient amount of thermal insulation to eliminate the potential for thermal damages of surrounding tissues during detachment, and since the connecting fiber is heated and broken at a location fully contained within the distal portion of the pusher member, the potential for releasing undesirable particles of materials into the bloodstream and consequent embolization in the bloodstream is virtually eliminated.

In one presently preferred embodiment, the invention accordingly provides for an apparatus for release and deployment of a therapeutic device within the vasculature of a patient, comprising an elongated, flexible pusher member having an interior lumen and a distal portion; a tubular collar detachably mounting the therapeutic device to the pusher member for placement of the therapeutic device within the vasculature, the tubular collar being expandable when heated and having a closed configuration engaging a proximal portion of the therapeutic device and an open configuration releasing the therapeutic device; and a heater disposed in the tubular collar of the pusher member for heating the tubular collar to cause the tubular collar to expand and release the therapeutic device for detaching and deploying the therapeutic device from the flexible pusher member when a desired placement of the therapeutic device within the vasculature is achieved. In one presently preferred aspect, the heater comprises an electrical resistance heater coil, and may further comprise a power supply and control unit (which may be combined in a single unit) to supply electrical current to the heater coil. In a first presently preferred implementation of the tubular collar, the tubular collar is formed from a shape memory material, which may for example be a shape memory polymer, or a shape memory alloy. In another presently preferred implementation of the tubular collar, the tubular collar is formed from a thermoplastic material. The therapeutic device may comprise a vasoocclusive device, such as a microcoil.

The present invention also provides for a method for release and deployment of a therapeutic device within the vasculature of a patient, wherein a therapeutic device is provided, to be placed within the vasculature of a patient; an elongated, flexible pusher member is provided, having an interior lumen, and a distal portion; a tubular collar is provided for detachably mounting the therapeutic device to the pusher member for placement of the therapeutic device within the vasculature, the tubular collar being expandable when heated and having a closed configuration engaging a proximal portion of the therapeutic device and an open configuration when heated releasing the therapeutic device; the therapeutic device is positioned at a desired placement within a patient's vasculature; and said tubular collar is heated to expand said tubular collar for detaching and deploying the therapeutic device from the flexible pusher member when a desired placement of the therapeutic device within a patient's vasculature is achieved. In a presently preferred aspect of the method, the step of heating the tubular collar comprises passing electrical current through the electrical resistance heater to expand the tubular collar.

In another presently preferred embodiment, the invention provides for an apparatus for release and deployment of a therapeutic device within the vasculature of a patient, which comprises an elongated, flexible pusher member having an interior lumen, and a connector fiber detachably mounting the therapeutic device to the pusher member for placement of the therapeutic device within the vasculature, the connector fiber being capable of being broken by heat. A heater is disposed adjacent to the connector fiber for heating the connector fiber to cause the connector fiber to break and release the therapeutic device for detaching and deploying the therapeutic device from the flexible pusher member when a desired placement of the therapeutic device within the vasculature is achieved. In one currently preferred aspect, the distal portion of the pusher member includes at least one entry port communicating with the interior lumen, with the heater disposed in the interior lumen of the pusher member adjacent to one or more entry ports. In another presently preferred aspect, the connector fiber passes through the heater. In a currently preferred embodiment, the heater comprises an electrical resistance heater coil, and may also comprise a control unit, with the heater connected by electrical connectors to the control unit for supplying electrical current to the heater coil. In presently preferred aspects of the apparatus, the flexible pusher member comprises a heat insulating shaft, and the connector fiber is formed from a thermoplastic material, such as polyethylene.

In one presently preferred embodiment, the therapeutic device to be placed within the vasculature of a patient is connected to an annular connector ring, and the connector fiber mounting the therapeutic device to the pusher member passes through the connector ring to secure the therapeutic device to the pusher member. In a currently preferred aspect, the connector fiber extends from a proximal portion of the pusher member to form a loop through the connector ring, and back through the one or more ports through the pusher member to the proximal portion of the pusher member. In another presently preferred aspect, the therapeutic device comprises a vasooclusive device, such as a microcoil.

The invention also provides for a method for release and deployment of a therapeutic device within the vasculature of a patient. In the method of the invention, a therapeutic device to be placed within the vasculature of a patient is provided; and an elongated, flexible pusher member. A connector fiber detachably mounts the therapeutic device to the pusher member for placement of the therapeutic device within the vasculature, with the connector fiber being capable of being broken by heating, and the therapeutic device is positioned at a desired placement within a patient's vasculature. Thereafter, a portion of the connector fiber is heated to break the portion of the connector fiber for detaching and deploying the therapeutic device from the flexible pusher member when a desired placement of the therapeutic device within a patient's vasculature is achieved. In a presently preferred aspect of the method, the portion of the connector fiber to be broken is passed through an electrical resistance heater disposed within the lumen of the flexible pusher member, and the step of heating the portion of the connector fiber comprises passing electrical current through the electrical resistance heater to break the portion of the connector fiber.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
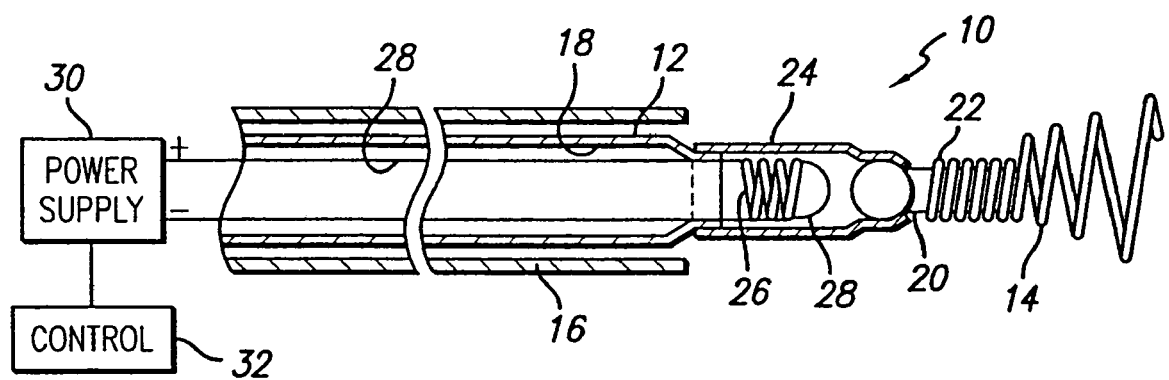
FIG. 1 is a side sectional view of a first embodiment of the apparatus for release and deployment of a therapeutic device.

While vasoocclusive devices have conventionally been delivered to a portion of a patient's vasculature to be treated through a delivery catheter by means of a pusher device, such conventional methods can involve separation of the vasoocclusive device from the pusher device in ways that result in injury to the vasculature, such as by causing thermal damage of surrounding tissues during detachment that can cause embolization in the bloodstream, or by release of undesirable particles of materials into the bloodstream that can cause embolization in the bloodstream.

As is illustrated in the drawings, in a first presently preferred embodiment, the invention is embodied in an apparatus for deployment of a therapeutic device such as a micro-coil using a catheter by connecting the therapeutic device to a distal portion of a pusher member by a tubular collar that can be expanded by heating a portion of the tubular collar to thereby release the therapeutic device for placement in the vasculature.

Figure 2:
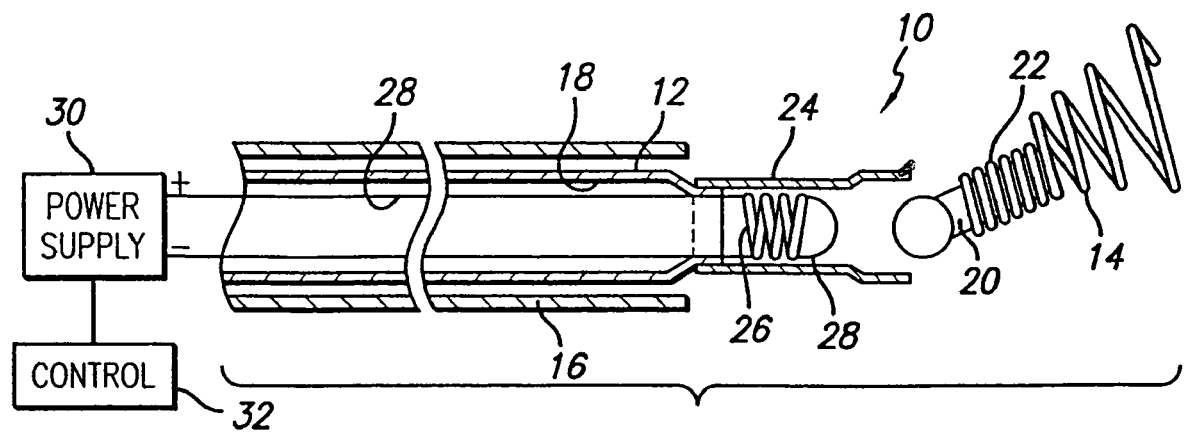
FIG. 2 is a side sectional view of the apparatus of FIG. 1, illustrating release of the therapeutic device upon heating of the tubular collar.
Figure 3:
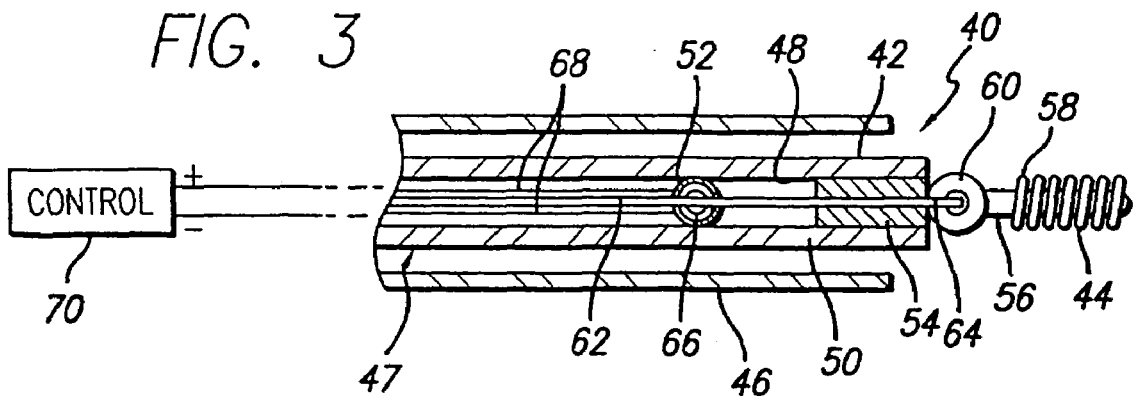
FIG. 3 is a top sectional view of a second embodiment of the apparatus for release and deployment of a therapeutic device.
Figure 4:
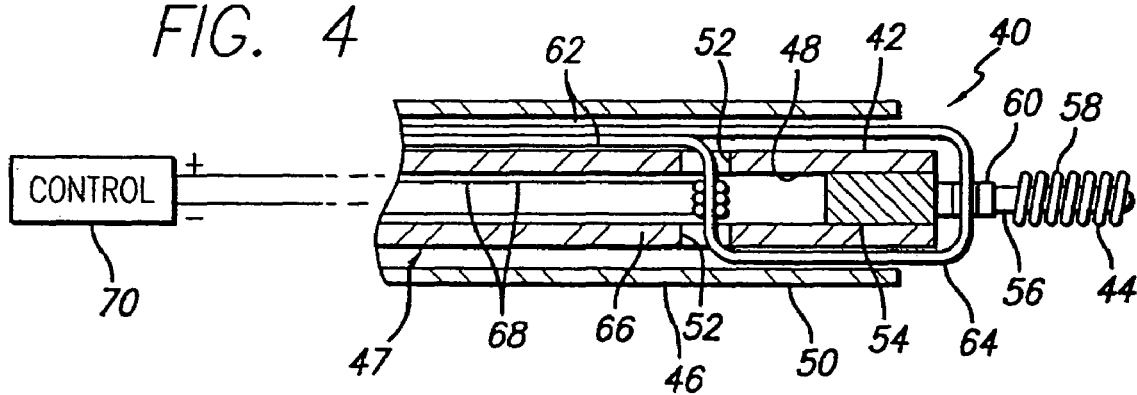
FIG. 4 is a side sectional view of the apparatus of FIG. 3.
Figure 5:
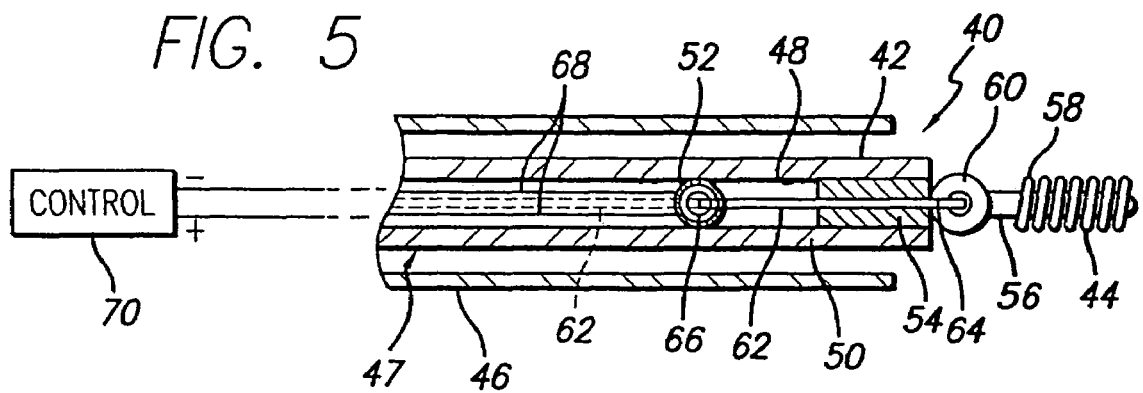
FIG. 5 is a bottom sectional view of the apparatus of FIG. 3.
Figure 6:
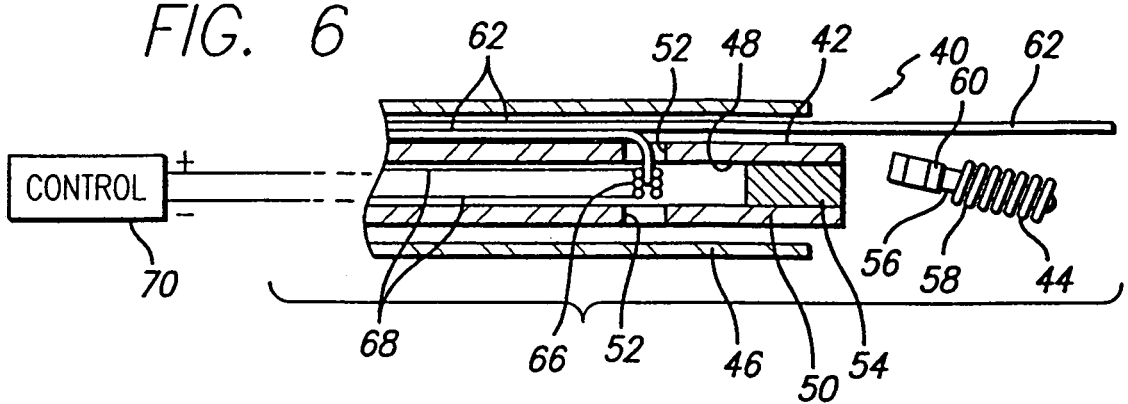
FIG. 6 is a side sectional view of the apparatus of FIG. 3, illustrating release of the therapeutic device upon heating of the elongated connector fiber.

With reference to FIGS. 1 and 2, the invention provides for an apparatus 10 including an elongated, flexible pusher catheter member 12 for release and deployment of a therapeutic device 14 such as a vasoocclusive device, and which may for example be a microcoil, only a portion of which is shown. The therapeutic device is typically released within the vasculature of a patient, introduced through a delivery catheter 16, for treatment of a target aneurysm. The pusher catheter member has a shaft defining an interior lumen 18. The therapeutic device is typically connected to a stem 20 such as by solder 22, for example, although welding or adhesive, or the like may also be suitable, and the therapeutic device is mounted and secured to the distal portion of the pusher catheter member by a tubular collar 24 crimped in a closed configuration about the proximal end of the stem of the therapeutic device, and mounted to the distal end of the pusher catheter, typically by adhesive, such as cyanoacrylate adhesive, for example.

In one presently preferred embodiment, the tubular collar is formed from a shape memory polymer (SMP), having a glass transition temperature (Td above body temperature, such as polyurethane, that can be heat treated to have shape memory behavior.

In another presently preferred embodiment, the collar can be made of polymers that are not shape memory polymers, such as polyethylene terephthalate (PET), polyolefins, fluorocarbons, high density polyethylene (HDPE), and other thermoplastic polymers.

In another presently preferred embodiment, the collar can be made of a shape memory alloy spring at the distal end of the catheter. The shape memory alloy can for example be a shape memory metal such as nickel titanium alloy, such as that available under the trade name NITINOL, for example, that can be heat treated to have shape memory behavior. When the current is applied through the connector, the shape memory alloy spring will transform from a martensitic state to an austenitic state, to release the coil socket from the shape memory alloy spring.

A heater, such as an electrical resistance heater coil 26, is disposed within the collar, and is connected by electrical connectors 28 extending through the lumen of the pusher catheter to a power supply 30 which can in turn be operated by a control unit 32. The power supply and control unit may optionally be combined. The resistance heater coil can be fabricated from platinum, stainless steel, or other high resistance materials, and the electrical connectors can be copper or other highly electrically conductive leads that extend to the proximal part of the pusher catheter assembly. The power supply may be quite small, housing a small battery, for example, that is sufficient to supply electrical current to the heater coil to cause the collar to expand due to the application of heat, and release the therapeutic device, as is illustrated in FIG. 2. Alternatively, the heater may deliver heat to the tubular collar by other means, such as thermo-mechanical, electromagnetic or RF energy, for example. The lumen and collar of the pusher catheter member advantageously provides an insulative space and wall thickness to contain the heating of the collar to avoid thermal damage to surrounding tissues during heating of the collar to deploy the therapeutic device. Additionally, most of the pusher catheter member is surrounded by a guiding or delivery catheter, so that the heating of the collar does not come in contact with tissue.

In another presently preferred embodiment, the invention is embodied in an apparatus for deployment of a therapeutic device such as a micro-coil using a catheter by connecting the therapeutic device to a distal portion of a pusher member by a connector fiber that can be broken by heating a portion of the connector fiber to break the connector fiber and thereby release the therapeutic device for placement in the vasculature.

With reference to FIGS. 3–6, in another presently preferred embodiment, the invention provides for an apparatus 40 including an elongated, flexible pusher member 42 for release and deployment of a therapeutic device 44 such as a vasoocclusive device, which may for example be a microcoil, only a portion of which is shown, within the vasculature of a patient, through a delivery catheter 46. The pusher member has a shaft 47 that provides a measure of thermal insulation to an interior lumen 48, as will be further explained below. The shaft of the pusher member typically has an outer diameter of approximately 0.015", and an inside diameter of approximately 0.007, and can be formed from polyethylene terephthalate (PET) tubing. The pusher member has a distal portion 50 with entry ports 52 in communication with the interior lumen, and a plug 54 at the distal end of the pusher member, typically secured within the distal end of the pusher member by adhesive, such as a cyanoacrylate adhesive, for example.

The therapeutic device is typically connected to a stem 56 such as by solder 58, and the stem is in turn connected to an annular connector ring 60, typically by an adhesive such as a cyanoacrylate adhesive, for example. The therapeutic device is mounted and secured to the distal portion of the pusher member by an elongated connector thread or fiber 62 extending from a proximal portion of the pusher member to form a loop 64 through the connector ring, and extending back through the entry ports of the pusher member to the proximal portion of the pusher member. In a presently preferred embodiment, the connector fiber is formed of polyethylene, and is typically about 0.015 to 0.030 inches in diameter, although the connector fiber can be as thin as about 0.0005 inches in diameter, and can be formed from a variety of thermoplastic materials with high tensile strength and suitable melt temperatures. The connector fiber may also optionally be formed of a suitable high tensile strength material, such as a biodegradable material, for example, that would merely degrade or decompose to break upon being heated.

A portion of the connector fiber to be broken to deploy the therapeutic device passes through a heater, such as a resistive heater coil 66 connected by electrical connectors 68 to a control unit 70 which supplies electrical current to the heater coil to cause the connector fiber to break and release the therapeutic device. Alternatively, the heater may deliver heat to the connector fiber by other means, such as thermo-mechanical, electromagnetic or RF energy, for example. The lumen of the pusher member advantageously provides an insulative space and wall thickness to contain the heating of the connector fiber to avoid thermal damage to surrounding tissues, and to help contain pieces of the connector fiber that may be formed during heating of the connector fiber to deploy the therapeutic device.

Figure 7:
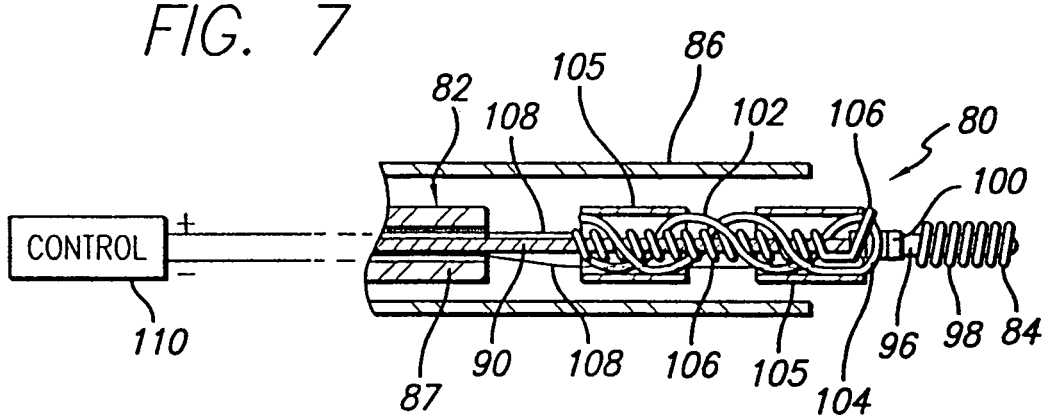
FIG. 7 is a side sectional view of a third embodiment of the apparatus for release and deployment of a therapeutic device.
Figure 8:
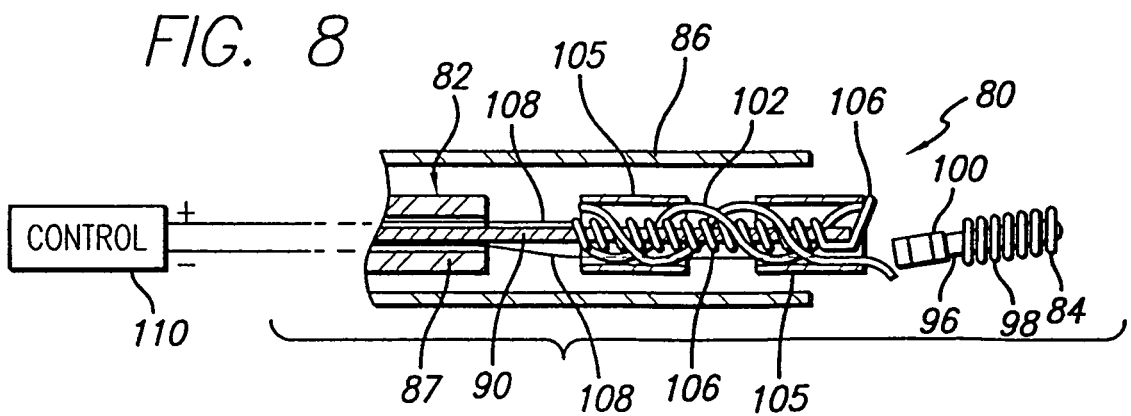
FIG. 8 is a side sectional view of the apparatus of FIG. 7, illustrating release of the therapeutic device upon heating of the elongated connector fiber.

With reference to FIGS. 7 and 8, in another presently preferred embodiment, the invention provides for an apparatus 80 including an elongated, flexible pusher catheter member 82 for release and deployment of a therapeutic device 84 such as a vasoocclusive device, which may for example be a microcoil, only a portion of which is shown, within the vasculature of a patient, through a guiding or delivery catheter 86. The pusher catheter member has a shaft 87 that is currently preferably formed from a PET lamination, and an inner elongated coaxial mandrel 90 typically formed of stainless steel, which may extend distally beyond the shaft of the pusher catheter member.

The therapeutic device is typically connected to a stem 96 such as by solder 98, and the stem is in turn connected to an annular connector ring 100, typically by an adhesive such as a cyanoacrylate adhesive, for example. The therapeutic device is mounted and secured to the distal portion of the pusher member by an elongated connector thread or fiber 102 extending distally from the pusher catheter member shaft over the distal portion of the mandrel to form a loop 104 through the connector ring, and extending back toward the pusher catheter member shaft. The elongated connector fiber is retained over the mandrel by one or more annular rings or collars 105, typically formed of PET. In a presently preferred embodiment, the connector fiber is formed of polyethylene, such as a medium density polyethylene, and is typically about 0.015 to 0.030 inches in diameter, although the connector fiber can be as thin as about 0.0005 inches in diameter, and can be formed from a variety of thermoplastic materials with high tensile strength and suitable melt temperatures. The connector fiber may also optionally be formed of a suitable high tensile strength material, such as a biodegradable material, for example, that would merely degrade or decompose to break upon being heated.

A portion of the connector fiber to be broken to deploy the therapeutic device passes through a heater, such as a resistive heater coil 106 connected by electrical connectors 108, typically formed by copper wire with a polyamide casing, extending to a control unit 110 which supplies electrical current to the heater coil to cause the connector fiber to break and release the therapeutic device. The heater coil preferably fits closely around the connector fiber. Alternatively, the heater may deliver heat to the connector fiber by other means, such as thermo-mechanical, electromagnetic or RF energy, for example. The lumen of the pusher member advantageously provides an insulative space and wall thickness to contain the heating of the connector fiber to avoid thermal damage to surrounding tissues, and to help contain pieces of the connector fiber that may be formed during heating of the connector fiber to deploy the therapeutic device.

Figure 9:
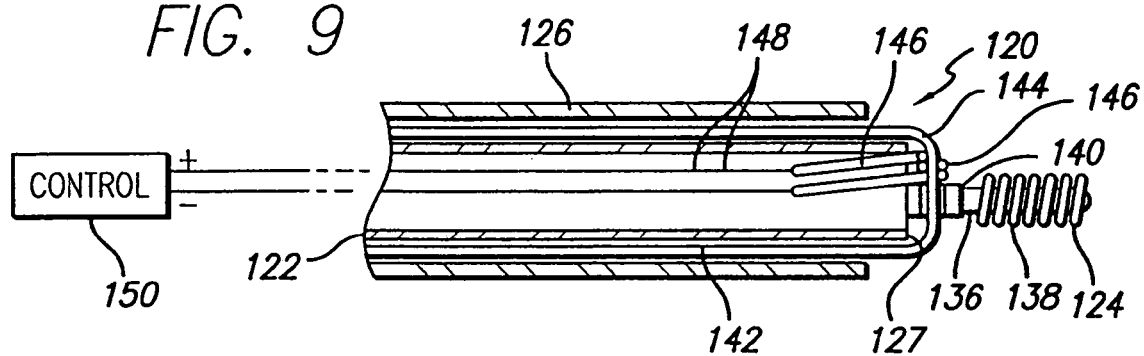
FIG. 9 is a side sectional view of a fourth embodiment of the apparatus for release and deployment of a therapeutic device.
Figure 10:
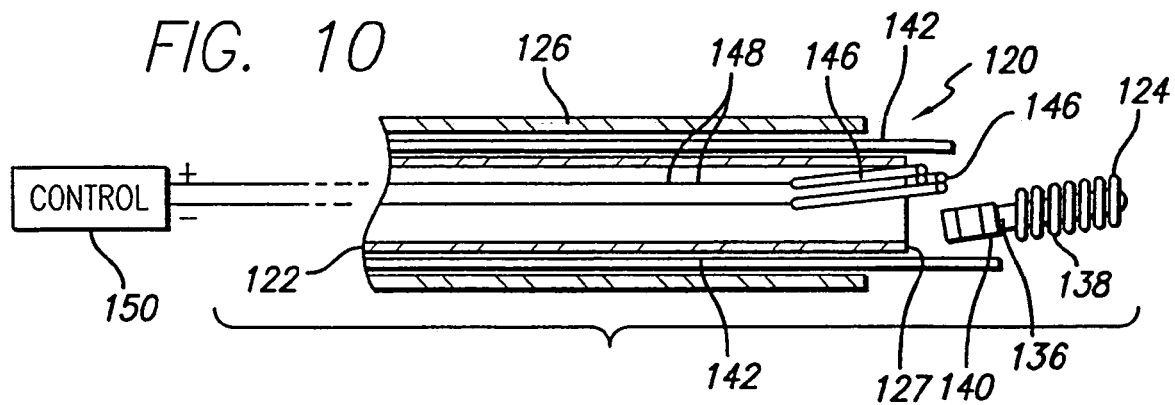
FIG. 10 is a side sectional view of the apparatus of FIG. 9, illustrating release of the therapeutic device upon heating of the elongated connector fiber.

With reference to FIGS. 9 and 10, in another presently preferred embodiment, the invention provides for an apparatus 120 including an elongated, flexible pusher catheter member 122 for release and deployment of a therapeutic device 124 such as a vasoocclusive device, which may for example be a microcoil, only a portion of which is shown, within the vasculature of a patient, through a guiding or delivery catheter 126. The pusher catheter member has a shaft 127 that is open at its distal end.

The therapeutic device is typically connected to a stem 136 such as by solder 138, and the stem is in turn connected to an annular connector ring 140, typically by an adhesive such as a cyanoacrylate adhesive, for example. The therapeutic device is mounted and secured to the distal portion of the pusher member by an elongated connector thread or fiber 142 extending distally over pusher catheter member shaft to form a loop 144 through the connector ring, and extending back proximally over the pusher catheter member shaft. In a presently preferred embodiment, the connector fiber is formed of polyethylene, such as a medium density polyethylene, and is typically about 0.015 to 0.030 inches in diameter, although the connector fiber can be as thin as about 0.0005 inches in diameter, and can be formed from a variety of thermoplastic materials with high tensile strength and suitable melt temperatures. The connector fiber may also optionally be formed of a suitable high tensile strength material, such as a biodegradable material, for example, that would merely degrade or decompose to break upon being heated.

A portion of the connector fiber to be broken to deploy the therapeutic device passes through a heater, such as a resistive heater coil 146 connected by electrical connectors 148 extending to a control unit 150 which supplies electrical current to the heater coil to cause the connector fiber to break and release the therapeutic device. The heater coil preferably fits closely around the connector fiber. Alternatively, the heater may deliver heat to the connector fiber by other means, such as thermo-mechanical, electromagnetic or RF energy, for example. The lumen of the pusher member advantageously provides an insulative space and wall thickness to contain the heating of the connector fiber to avoid thermal damage to surrounding tissues, and to help contain pieces of the connector fiber that may be formed during heating of the connector fiber to deploy the therapeutic device.

It will be apparent from the foregoing that while particular forms of the invention have been illustrated and described, various modifications can be made without departing from the spirit and scope of the invention. Accordingly, it is not intended that the invention be limited, except as by the appended claims.

The invention claimed is:

1. An apparatus for release of a therapeutic device within the vasculature of a patient, comprising:
    an elongated, flexible pusher member having a distal end;
    an elongated coaxial mandrel disposed in said elongated, flexible pusher member and having a distal portion extending beyond the distal end of the elongated, flexible pusher member;
    a connector fiber connecting the therapeutic device to the pusher member disposed over said distal portion of said elongated coaxial mandrel and having a distal portion extending beyond said distal portion of said elongated coaxial mandrel, the connector fiber being capable of being broken by heat;

at least one annular collar disposed over said connector fiber and said distal portion of said mandrel and retaining said connector fiber on said mandrel; and a heater disposed adjacent to the connector fiber for heating the connector fiber to cause the connector fiber to break and release the therapeutic device and to detach the therapeutic device from the flexible pusher member when a desired placement of the therapeutic device within the vasculature is achieved.

2. The apparatus of claim 1, wherein said heater comprises an electrical resistance heater coil.

3. The apparatus of claim 1, further comprising a control unit, and wherein said heater is connected by electrical connectors to the control unit which supplies electrical current to the heater.

4. The apparatus of claim 1, wherein said flexible pusher member comprises a heat insulating shaft.

5. The apparatus of claim 1, wherein said connector fiber is formed from a thermoplastic material.

6. The apparatus of claim 1, wherein said connector fiber is formed from polyethylene.

7. The apparatus of claim 1, wherein said connector fiber passes through the heater.

8. The apparatus of claim 1, wherein said therapeutic device to be placed within the vasculature of a patient is connected to an annular connector ring, and the connector fiber passes through the connector ring to connect the therapeutic device to the pusher member.

9. The apparatus of claim 1, wherein said therapeutic device comprises a vasoocclusive device.

10. The apparatus of claim 1, wherein said therapeutic device comprises a microcoil.

11. The apparatus of claim 1, wherein said at least one annular collar is formed of polyethylene terephthalate.

* * * * *